United States Patent

Ogata et al.

Patent Number: 5,474,992
Date of Patent: Dec. 12, 1995

[54] METHOD OF TREATMENT WITH PHARMACEUTICAL COMPOSITION FOR RENAL DISORDER AND A DIALYSIS SOLUTION FOR EXTRACORPOREAL HEMODIALYSIS

[75] Inventors: Kazumi Ogata, Toyonaka; Takahiro Sakaue, Itami; Noriko Saito, Minoo; Sachiko Matsuura, Osaka; Rie Nagao, Neyagawa; Shinya Ogino, Itami, all of Japan

[73] Assignee: Senju Pharmaceutical Co., Ltd., Osaka, Japan

[21] Appl. No.: 302,192

[22] Filed: Aug. 31, 1994

[30] Foreign Application Priority Data

Sep. 10, 1993 [JP] Japan ..................... 5-225389

[51] Int. Cl.$^6$ ............... A61K 31/665; A61K 31/66; A61K 31/355
[52] U.S. Cl. ............ 514/100; 514/120; 514/129; 514/141
[58] Field of Search ............ 514/310, 100, 514/120, 129; 549/220; 426/545, 547

[56] References Cited

U.S. PATENT DOCUMENTS

| | | | |
|---|---|---|---|
| 4,948,786 | 8/1990 | Shimamoto et al. | 514/100 |
| 5,306,913 | 4/1994 | Suetsugu et al. | 514/100 |

Primary Examiner—Arthur C. Prescott
Attorney, Agent, or Firm—Wenderoth, Lind & Ponack

[57] ABSTRACT

A pharmaceutical composition for renal disorder and a dialysis solution for extracorporeal hemodialysis which comprise a phosphoric acid diester of the following formula:

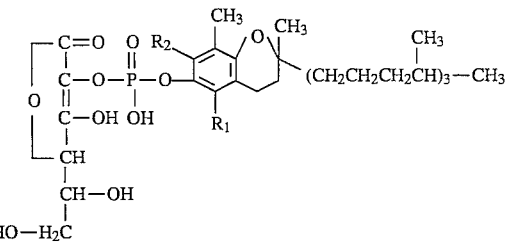

(wherein $R_1$ and $R_2$ are the same or different and each represents a hydrogen atom or a methyl group) or a pharmacologically acceptable salt thereof.

Since the composition of this invention inhibits the formation of free radicals in the body, it can be advantageously used for the prophylaxis and treatment of various renal disorders such as glomerulonephritis, acute renal failure, uremia, adriamycin nephrosis, puromycin nephrosis, gentamicin- and cisplatin-induced disorders of the kidney, renal impairment due to paraquat and other agricultural chemicals, and immune complex nephritis. Moreover, the composition of this invention is also of use as a dialysis solution for extracorporeal hemodialysis with the propylactic/therapeutic effect on dialysis amyloidosis.

7 Claims, No Drawings

METHOD OF TREATMENT WITH PHARMACEUTICAL COMPOSITION FOR RENAL DISORDER AND A DIALYSIS SOLUTION FOR EXTRACORPOREAL HEMODIALYSIS

BACKGROUND OF THE INVENTION

1. Field of the Invention

This invention relates to a useful pharmaceutical composition for the therapy of renal disorder and a dialysis solution for extracorporeal hemodialysis. More particularly, this invention relates to a useful pharmaceutical composition for the therapy of renal disorder and a dialysis solution for extracorporeal hemodialysis each comprising an ascorbyl tocopheryl diester of phosphoric acid or a pharmacologically acceptable salt thereof.

2. Description of the Prior Art

It is known that the active oxygen species and free radicals formed in the body may cause aging and a broad spectrum of diseases inclusive of malignant neoplasms. The kidney, in particular, is highly relevant to such active oxygen species and free radicals because of the vital physiological functions assigned to this organ. In the kidney, literally all toxic substances, drugs and so on are pooled for excretion or reabsorption. As a result, the free radicals formed directly from such substances cause renal disorders. Moreover, a variety of substances including immune complexes in the circulation stimulate the neutrophils and macrophages to release active oxygen species which damage the glomeruli. In addition to kidney disorders due to such blood factors, the role which free radicals play as a causative and exacerbating factor in nephritis through the autoimmune system is attracting attention. In the current drug therapy of nephritis and other disorders of the kidney, various immunosuppressants, drugs having antiplatelet activity, and antiinflammatory drugs are in common use clinically and, in fact, free radical formation inhibitory activity has been discovered in some of these drugs. However, none of them are considered fully satisfactory in terms of the action potential to inhibit free radical formation.

Meanwhile, chronic hemodialysis induces dialysis amyloidosis in the patient on dialysis treatment. As a therapeutic approach, the use of a high-performance dialysis membrane is gaining popularity for eliminating $\beta_2$-microglobulin ($\beta_2$-MG) which is a causative agent of amyloidosis. However, when this dialysis treatment is performed chronically, symptomatic aggravations are sometimes experienced despite improvements in the $\beta_2$-MG picture and it has been pointed out that free radicals are involved in the onset of dialysis amyloidosis as well. However, it is the state of the art that there is not known a dialysis solution for extracorporeal hemodialysis which is effective for the prevention and treatment of amyloidosis.

Under the circumstances, a real demand exists in the art for a drug and a hemodialysis solution which would successfully inhibit the formation of, or scavenge, free radicals in vivo and, as such, be useful for the prophylaxis and therapy of various disorders of the kidney.

The inventors of this invention long studying the pharmacological actions of ascorbyl tocopheryl diester of phosphoric acid discovered that this compound effectively inhibits the formation of free radicals in the body and scavenges them and is of value as a therapeutic drug for renal disorder or a dialysis solution for extracorporeal hemodialysis. This invention has been developed on the basis of the above findings.

SUMMARY OF THE INVENTION

This invention is, therefore, directed to:

(1) a pharmaceutical composition for renal disorder which comprises a phosphoric acid diester of the following formula:

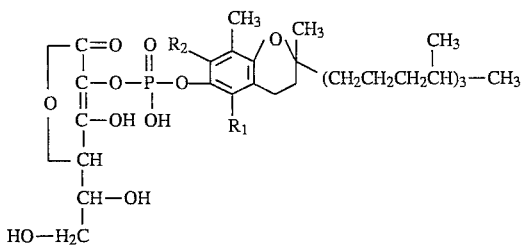

(wherein $R_1$ and $R_2$ are the same or different and each represents a hydrogen atom or a methyl group) or a pharmacologically acceptable salt thereof (hereinafter referred to collectively as the compound of this invention);

(2) the pharmaceutical composition for renal disorder as defined under (1), wherein the renal disorder is a disease selected from the group consisting of glomerulonephritis, acute renal failure, uremia, adriamycin nephrosls, puromycin nephrosls, gentamicin-, cisplatin- and paraquat-induced disorders of the kidney and immune complex nephritis;

(3) the pharmaceutical composition for renal disorder as defined under (1) as provided in the dosage form of a peroral tablet or an injection;

(4) a dialysis solution for extracorporeal hemodialysis which comprises the phosphoric acid diester or pharmacologically acceptable salt as defined under (1);

(5) the dialysis solution for extracorporeal hemodialysis as defined under (4) which comprises said phosphoric acid diester or pharmacologically acceptable salt in a concentration of 0.001 to 0.05 (w/v) %; and (6) the dialysis solution for extracorporeal hemodialysis as defined under (4) or (5) which has an osmotic pressure of 270 to 300 mOsm/kgH$_2$O and a pH value of 6 to 8.

DETAILED DESCRIPTION OF THE INVENTION

The compound for use in the pharmaceutical composition for renal disorder or the dialysis solution for extracorporeal hemodialysis in accordance with this invention can be synthesized by the process described in the specification of Japanese Patent Publication H- 2-44478 or in the specification of Japanese Patent Application Kokai S-62-205091, or any process analogous therewith, among others.

It is already known that the compound of this invention for use in the pharmaceutical composition for renal disorder or the dialysis solution for extracorporeal hemodialysis is of use as an anticataract agent, a prophylactic and therapeutic agent for climacteric disturbance, a skin care cosmetic ingredient (Japanese Patent Publication H-2-44478), an antiinflammatory agent (Japanese Patent Publication H-1-27044), an antiulcer agent (Japanese Patent Application Kokai S-63-270626), and a prophylactic and therapeutic agent for ischemic organic disorders (Japanese patent Application Kokai H-2-111722), among others.

The compound of this invention for use in the pharmaceutical composition for renal disorder or in the dialysis solution for extracorporeal hemodialysis can be used in either the free form or in the form of a pharmacologically acceptable salt thereof. The pharmacologically acceptable salt that can be used includes salts with alkali metals such as sodium, potassium, etc. and salts with alkaline earth metals such as calcium and magnesium, among others. Other types of salts, if acceptable from the pharmacologic point of view, can also be employed.

The pharmaceutical composition for renal disorder and the dialysis solution for extracorporeal hemodialysis according to this invention may contain one or more species of the compound of this invention according to the intended use.

The compound of this invention for use as the active ingredient of said pharmaceutical composition or dialysis solution is extremely low in toxicity and highly safe and, therefore, can be used advantageously for purposes of this invention [e.g. the $LD_{50}$ values of L-ascorbyl DL-α-tocopheryl phosphate potassium (hereinafter referred to briefly as EPC-K)≧5 g/kg p.o. (rats) and≧100 mg/kg i.v. (rats)].

The pharmaceutical composition for the treatment of renal disorder can be administered orally or parenterally. The dosage form includes a variety of solid preparations such as tablets, granules, powders, capsules, etc. and a variety of liquid preparations such as injections, and such dosage forms can be manufactured by the per se known procedures. In the manufacture, various pharmaceutical additives which are commonly employed, such as an excipient, binder, disintegrator, dispersant, reabsorption promoter, buffer, surfactant, solubilizer, preservative, emulsifier, isotonizing agent, stabilizer, pH control agent, etc., can be incorporated in suitable amounts.

The dialysis solution for extracorporeal hemodialysis according to this invention is manufactured in the form of a suitable solution by the per se known procedure. The osmotic pressure and pH of the liquid preparation are preferably adjusted within the respective ranges for hemodialysis solutions in general. For example, the osmotic pressure is about 270 to 300 mOsm/KgH$_2$O, preferably about 280 to 290 mOsm/kgH$_2$O, and the preferred pH is about 6 to 8. Such a liquid preparation may contain a variety of other ingredients which are generally included in dialysis solutions for extracorporeal hemodialysis, for example various salts such as sodium chloride, potassium chloride, calcium chloride, magnesium chloride, sodium acetate, sodium hydrogen carbonate, etc. and saccharides such as glucose In the usual amounts. If necessary, the dialysis solution may be supplied in a solid dosage form, e.g. tablet, granule, powder, etc, for extemporaneous reconstitution.

The artificial kidney dialysis solution thus manufactured in accordance with this invention can be applied to dialysis treatment using a conventional extracorporeal hemodialyzer of the hollow fiber (HFK), kiil (plate) or coil type. Each of such dialyzers dialysate comprises a blood compartment and a dialysate compartment as partitioned by a semipermeable membrane (dialysis membrane) of e.g. cellulose or polymethyl methacrylate (PMMA), which are communicating with a blood line and a dialysate line, respectively, in a loop. The desired dialysis treatment can be accomplished by allowing the substances to be removed from the blood to migrate into the dialysis solution across the dialysis membrane.

The dosage of the compound of this invention as a therapeutic agent for renal disorder is dependent on species of the compound, type of renal disorder to be treated, the patient's age and body weight, the symptoms to be controlled, and dosage form. Taking an injection as an example, about 1 to 100 mg is administered once a day in adults. In the case of an oral preparation, 10 to 1000 mg is administered a few times a day in adult cases.

The concentration of the compound of this invention in the dialysis solution for extracorporeal hemodialysis is dependent on species of the compound, dialysis time, the patient's age and body weight, the symptoms to be controlled, and other conditions. Generally, a concentration of about 0.001 to 0.05 (w/v) % or preferably about 0.005 to 0.02 (w/v) % is recommended.

Unless contrary to the objects of this invention, the pharmaceutical composition and dialysis solution of this invention may contain other therapeutic agents for renal disorder and/or agents expected to produce other pharmacological effects.

EXAMPLES

The following experimental examples and formulation examples are further illustrative of this invention.

[Experimental Example 1] Effect of the compound of this invention on renal impairment in rats with vitamin E deficiency The effect of the compound of this invention, administered orally, on renal impairment in rats with vitamin E deficiency was evaluated.

Test substance: L-ascorbyl DL-α-tocopheryl phosphate potassium (abbreviation: EPC-K).

Method: Male Wistar rats were purchased from Japan Clea, Inc. at the age of 4 weeks and put on a vitamin E-deficient diet for 10 weeks before the experiment.

The rat model of renal impairment was constructed by administering 1 mmol/kg of DL-buthionine sulfoximine (abbreviation: BSO), a glutathione (abbreviation: GSH) synthesis inhibitor, intraperitoneally once a day for 3 consecutive days.

Five hours after the last administration of DL-buthionine sulfoximine (BSO), the blood was drawn from the lower abdominal aorta under pentobarbital anesthesia and the serum levels of creatinine, urea nitrogen (abbreviation: BUN) and lipid peroxide (abbreviation: LPO), which are indicators of renal function, were determined by Jaffe's method, urease-indophenol method, and Yagi's method, respectively.

The test substance EPC-K was administered orally in a dose of 141 mg/5 ml/kg once daily for one week until the blood sampling day. As a control, distilled water was used.

Results: The results are shown in Table 1.

TABLE 1

| Effect of the compound of this invention on renal impairment in rats with vitamin E deficiency | | | |
|---|---|---|---|
| group | Creatinine (mg/dl) | BUN (mg/dl) | LPO (nmol/ml) |
| Distilled water | 5.8 ± 0.2 | 208.5 ± 17.7 | 5.4 ± 0.9 |
| EPC-K | 2.0 ± 1.3* | 62.5 ± 37.1** | 3.8 ± 0.1 |

Each value is the mean ± standard error. The number of cases is 5 per group.

*; $p < 0.05$,
**; $p < 0.01$.

Generally when DL-buthionine sulfoximine (BSO), a glutathione (GSH) synthesis inhibitor, is administered to rats with vitamin E deficiency, the kidney hypertrophies and renal disorder develops. As the kidney is impaired, its excretory function is adversely affected and because of the consequent retention of urine components in the blood, urea nitrogen (BUN) and creatinine levels are elevated. Moreover, in vitamin E deficiency, the formation of lipid peroxide (LPO) in the body is promoted. On the other hand, glutathione (GSH) may augment the inhibitory effect of vitamin E on the bioformation of LPO and when GSH is depleted in vitamin E deficiency, the bioformation of LPO is further encouraged.

It is apparent from Table 1 that the composition of this invention on oral administration does effectively inhibit elevation of serum urea nitrogen (BUN), creatinine and lipid peroxide (LPO), all of which are indicators of renal function, suggesting that it is of great use as a therapeutic agent for renal disorder and a dialysis solution for extracorporeal hemodialysis.

Furthermore, pathological examination of the treated kidney revealed alleviation of changes such as necrosis and exfoliation of tubular epithelial cells, suggesting a significant effect on renal impairment.

[Experimental Example 2] Effect of the compound of this invention on adriamycin nephrosis in rats The effect of the compound of this Invention on adriamycin nephrosis in rats was evaluated.

Test substance: EPC-K

Method: This study was conducted in male SD rats (body weight: about 180 g) purchased from Japan SLC. The rats were intravenously dosed with 7.5 mg/kg of adriamycin to induce renal impairment.

The test substance EPC-K was administered intraperitoneally once daily and the rat was sacrificed on day 80 for determination of biochemical parameters. Physiological saline was used as control.

Results: The results are shown in Table 2.

TABLE 2

Effect of the compound of this invention on adriamycin nephrosis in rats

| group | BUN (mg/dl) | Creatinine (mg/dl) | LPO (nmol/ml) | Urinary protein (mg/day) |
|---|---|---|---|---|
| Control (saline) | 23.5 ± 1.7 | 0.50 ± 0.28 | 2.5 ± 1.8 | 696 ± 710 |
| EPC-K (1 mg/kg, i.p.) | 18.2 ± 1.2* | 0.30 ± 0 | 1.4 ± 0.8 | 119 ± 54 |

Each value is the mean ± standard error. The number of cases is 5 to 6 per group.
*; $p < 0.0001$.

It is clear from Table 2 that the compound of this invention is effective in controlling the elevation of various biochemical parameter values in rats with adriamycin nephrosis, suggesting that it is useful for the treatment of adriamycin nephrosis.

[Experimental Example 3] Effect of the compound of this invention on salt-sensitive rats The effect of the compound of this invention on salt-sensitive rats was investigated.

Test substance: EPC-K

Method: Male Dahl S rats (salt-sensitive rats) were purchased from Seiwa Experimental Animal Institute and loaded with 8% aqueous solution of sodium chloride to induce renal impairment.

The test substance EPC-K was administered once daily for 4 weeks. As a control, distilled water was orally administered.

Results: The results are shown in Table 3.

TABLE 3

Effect of the compound of this invention on salt-sensitive rats

| group | BUN (mg/dl) |
|---|---|
| Control (5 ml/kg, p.o.) | 30.0 ± 2.9 |
| EPC-K (141 mg/kg, p.o.) | 18.5 ± 2.1* |
| EPC-K (5 mg/kg, i.p.) | 15.6 ± 2.7* |

Each value is the mean ± standard error. The number of cases is 4 to 6 per group.
*; $p < 0.0001$.

It is apparent from Table 3 that the compound of this invention significantly inhibits the elevation of serum urea nitrogen (BUN) level in salt-sensitive rats.

[Experimental Example 4] Effect of the compound of this invention on adenine nephrosis in rats The effect of the compound of this invention on adenine nephrosis in rats was evaluated.

Test substance: EPC-K

Method: Male Wistar rats, aged 7 weeks, were purchased from SLC and used.

The rats were put on a 0.5% adenine-containing diet for 30 days to induce adenine nephrosis.

The test substance EPC-K was intraperitoneally administered once a day. Physiological saline was used as control.

Results: The results are shown in Table 4.

TABLE 4

Effect of the compound of this invention on adenine nephrosis in rats

| group | BUN (mg/dl) | Creatinine (mg/dl) |
|---|---|---|
| Control (saline) | 98.4 ± 34.5 | 1.95 ± 0.64 |
| EPC-K (5 mg/kg, i.p.) | 61.5 ± 13.2* | 1.14 ± 0.32* |
| (10 mg/kg, i.p.) | 40.2 ± 5.2** | 0.73 ± 0.15** |
| Normal | 18.9 ± 1.6 | 0.39 ± 0.06** |

Each value is the mean ± standard error. The number of cases is 8 to 9 per group.
*; $p < 0.05$,
**; $p < 0.01$.

It is apparent from Table 4 that the compound of this invention significantly inhibits elevation of serum urea nitrogen (BUN) and creatinine levels in rats with adenine nephrosis.

[Experimental Example 5] Chemiluminescence assay of the scavenging effect of the drug on the neutrophil-derived active oxygens formed due to the dialysis membrane The scavenging effect of the compound of this invention on the neutrophil-derived active oxygens formed due to the dialysis membrane was evaluated by the chemiluminescence assay.

Test compound: EPC-K
Material:

| Dialysis Membrane | Artificial kidney (for clinical use) | Membrane material | Manufacturer |
|---|---|---|---|
| | Filtrizer (B2-1, 5H) | Polymethyl methacrylate | Toray Industries, Inc. |

---continued

Test substance: EPC-K
Instrument:
Photon counter      Distributor

Lumat(registered    Berthold
Trademark)(LB 9501)

Methods

1. Preparation of a neutrophil suspension

An SD rat was intraperitoneally infused with 120 ml/kg of 1% casein-containing Krebs-Ringer bicarbonate buffer ($Ca^{2+}$-free) and kept as it was for 15 to 18 hours. Then, ice-cooled phosphate buffered saline ($Ca^{2+}/Mg^{2+}$-free, briefly PBS) was infused into the peritoneal cavity and after massaging the abdomen, laparotomy was performed to collect the peritoneal fluid. This fluid was centrifuged (4° C.) at 150G for 5 minutes and the sediment was subjected to hemolysis treatment, washed with 2 portions of PBS and suspended in Hanks buffered saline ($Ca^{2+}/Mg^{2+}$-free; abbreviation: HBS) at a concentration of $5 \times 10^6$ cells/ml.

2. Preparation of a membrane material suspension (a suspension of PMMA)

The hollow fiber of polymethyl methacrylate (PMMA) was taken out from the Filtrizer cartridge, rinsed and dried. The dried hollow fiber was milled in a mortar (to a particle diameter of about 20 to 100 μm) and suspended in HBS at a concentration of 100 mg/ml.

3. Preparation of a luminescence reagent (a solution of MCLA)

MCLA (2-methyl-6-[p-methoxyphenyl]-3,7,-dihydroimidazolo[ 1,2-a]pyrazin-3-one)(Cypridina luciferin analog; manufactured by Tokyo Kasei Kogyo Co., Ltd.) was dissolved in HBS at a concentration of 5 μM.

4. Effect of the test substance, 1 μM, 3 μM or 10 μM, on the chemiluminescence due to neutrophil-derived active oxygens EPC-K was dissolved in HBS at final concentrations of 1 μM to 10 μM. To 100 μl of each solution were added 300 μl of the neutrophil suspension and 100 μl of the MCLA solution and the mixture was incubated at 37° for 10 minutes. Then, 20 μl of the PMMA suspension was added and the resulting MCLA-dependent chemiluminescence was quantitated in 5 replicates. From the photon count at maximal emission was subtracted the minimal count immediately following addition of the PMMA suspension to arrive at the chemiluminescence photon count (CPM). The count obtained with HBS (blank test) was compared with the count obtained with the drug and the percent inhibition (%) was calculated by means of the following equation.

$$\text{Percent inhibition (\%)} = \frac{\text{Count for blank} - \text{Count for drug}}{\text{Count for blank}} \times 100$$

Results: The results are shown in Table 5.

Table 5

Effect of the compound of this invention on neutrophil-derived active oxygens formed due to the dialysis membrane

| Drug | Concentration | Chemiluminescence photon count (CPM) | Percent inhibition (%) |
|---|---|---|---|
| EPC-K | 10 μM | 14518 ± 3648 | 65.8 |
| | 3 μM | 26800 ± 3057 | 36.8 |
| | 1 μM | 32230 ± 6949 | 24.0 |
| Blank test | — | 42392 ± 12789 | — |

Each value is the mean ± standard deviation. The number of cases is 5 per group.

It is apparent from Table 5 that the compound of this invention effectively inhibits the neutrophil-derived active oxygens formed due to the dialysis membrane and is, therefore, of use as a dialysis solution for extracorporeal hemodialysis.

[Formulation Example 1] Peroral tablets

| EPC-K | 100 mg |
|---|---|
| Lactose | 75 mg |
| Starch | 20 mg |
| Polyethylene glycol 6000 | 5 mg |

The above components are blended and compressed into a tablet in the conventional manner. Where necessary, the tablet may be sugar-coated.

[Formulation Example 2] Injection

| EPC-K | 200 mg |
|---|---|
| Mannitol | 5.0 g |
| 1N-Sodium hydroxide | q.s. |
| Distilled water | To make 100 ml |
| | pH 6.5 |

The above components are admixed and filtered through a membrane filter. The filtrate is aseptically filled in glass ampules, 5 ml per ampule, following by fusion-sealing to provide an injection.

[Formulation Example 3] Dialysis solution for extracorporeal hemodialysis

| EPC-K | 0.05 g |
|---|---|
| Sodium chloride | 4.0 g |
| Potassium chloride | 0.11 g |
| Calcium chloride (dihydrate) | 0.13 g |
| Magnesium chloride (hexahydrate) | 0.11 g |
| Sodium citrate (trihydrate) | 1.0 g |
| Sodium acetate | 2.0 g |
| Glucose | 1.4 g |
| 0.1N-Sodium hydroxide | q.s. |
| Distilled water | To make 100 ml |
| | pH 7.2 |

Using the above components, a dialysis solution for extracorporeal hemodialysis is manufactured in the per se conventional manner. This solution is extemporaneously diluted 7-fold.

The composition of this invention can be used with advantage for the prophylaxis and therapy of various disorders such as glomerulonephritis, acute renal failure, uremia, adriamycin nephrosis, puromycin nephrosis, gentamicin- and cisplatin-induced disorders of the kidney, renal impairment due to paraquat and other agricultural chemicals, and immune complex nephritis. Moreover, the composition of this invention is also of use as a dialysis solution for extracorporeal hemodialysis with the prophylactic/therapeutic effect on dialysis amyloidosis.

What is claimed is:

1. A method for the prophylaxis and treatment of a renal disorder which comprises administering orally or parenterally to a patient in need thereof a renal disorder inhibitory effective amount of a phosphoric acid diester of the following formula:

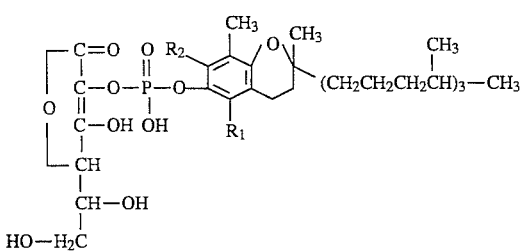

wherein $R_1$ and $R_2$ are the same or different and each represents a hydrogen atom or a methyl group or a pharmacologically acceptable salt thereof.

2. The method according to claim 1, wherein the renal disorder is a disease selected from the group consisting of glomerulonephritis, acute renal failure, uremia, adriamycin nephrosis, puromycin nephrosis, gentamicin-, cisplatin- and paraquat-induced disorders of the kidney and immune complex nephritis.

3. The method as claimed in claim 1, wherein the dose per administration is in the range of 10 to 1,000 mg for oral administration or 1 to 100 mg for injection.

4. A method for dialyzing the blood of a patient in need of such treatment which comprises employing as a dialysis solution flowing in an extracorporeal hemodialyzer a solution containing a free radical inhibitory effective amount of a phosphoric acid diester of the following formula:

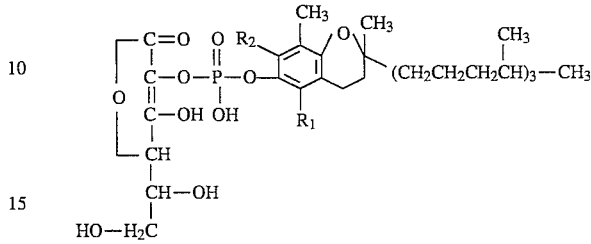

wherein $R_1$ and $R_2$ are the same or different and each represents a hydrogen atom or a methyl group or a pharmacologically acceptable salt thereof.

5. The method as claimed in claim 4, wherein the concentration of the compound or pharmacologically acceptable salt in the solution is in the range of 0.001 to 0.05 (w/v) %.

6. The method as claimed in claim 4, wherein the osmotic pressure is in the range of 270 to 300 mOsm/kgH$_2$O and the pH is in the range of 6 to 8.

7. The method as claimed in claim 5, wherein the osmotic pressure is in the range of 270 to 300 mOsm/kgH$_2$O and the pH is in the range of 6 to 8.

* * * * *